(12) United States Patent  
Nishizaki

(10) Patent No.: US 8,548,179 B2  
(45) Date of Patent: Oct. 1, 2013

(54) HEARING AID FITTING DEVICE

(75) Inventor: Makoto Nishizaki, Tokyo (JP)

(73) Assignee: Panasonic Corporation, Osaka (JP)

( * ) Notice: Subject to any disclaimer, the term of this patent is extended or adjusted under 35 U.S.C. 154(b) by 14 days.

(21) Appl. No.: 13/306,337

(22) Filed: Nov. 29, 2011

(65) Prior Publication Data

US 2012/0070023 A1    Mar. 22, 2012

Related U.S. Application Data

(63) Continuation of application No. PCT/JP2011/002282, filed on Apr. 19, 2011.

(30) Foreign Application Priority Data

Apr. 19, 2010 (JP) .................................. 2010-095671  
Sep. 8, 2010 (JP) .................................. 2010-200655

(51) Int. Cl.  
*H04R 25/00* (2006.01)

(52) U.S. Cl.  
USPC ............................ 381/314; 381/312; 381/315

(58) Field of Classification Search  
USPC ..................... 381/60, 312, 320–321, 314–316  
See application file for complete search history.

(56) References Cited

U.S. PATENT DOCUMENTS

| | | | |
|---|---|---|---|
| 4,972,487 | A | 11/1990 | Mangold et al. |
| 7,242,777 | B2 | 7/2007 | Leenen et al. |
| 2001/0005420 | A1 | 6/2001 | Takagi et al. |
| 2004/0066944 | A1 | 4/2004 | Leenen et al. |
| 2004/0131195 | A1 | 7/2004 | Mergell |
| 2006/0126872 | A1 | 6/2006 | Allegro-Baumann et al. |
| 2009/0279726 | A1 | 11/2009 | Baskent |
| 2011/0164772 | A1 | 7/2011 | Nishizaki et al. |
| 2011/0243355 | A1 | 10/2011 | Schmitt et al. |

FOREIGN PATENT DOCUMENTS

| | | |
|---|---|---|
| EP | 1 670 285 | 6/2006 |
| EP | 2 334 101 | 6/2011 |
| JP | 2-43900 | 2/1990 |
| JP | 8-317495 | 11/1996 |
| JP | 2000-125396 | 4/2000 |
| JP | 2001-175637 | 6/2001 |
| JP | 2001-204098 | 7/2001 |
| JP | 2003-339760 | 12/2003 |
| JP | 4525856 | 8/2010 |
| WO | 2007/045276 | 4/2007 |
| WO | 2008/151625 | 12/2008 |
| WO | 2009/022021 | 2/2009 |

OTHER PUBLICATIONS

Supplementary European Search Report issued Mar. 12, 2012 in Application No. EP 11 77 1746.

*Primary Examiner* — Suhan Ni  
(74) *Attorney, Agent, or Firm* — Wenderoth, Lind & Ponack, L.L.P.

(57) ABSTRACT

This hearing aid fitting device (1) comprises a client data storage section (10) that stores a plurality of hearing ability data and hearing adjustment result data for each of hearing ability data, a close user determination section (11) to which the client data storage section (10) and a hearing ability input section (12) are connected on the input side, a clustering section (13) that is connected to the output side of the close user determination section (11), a representative characteristic determination section (14) that is connected to the output side of the clustering section (13), an initial adjustment candidate selector (15) that is connected to the input side of the representative characteristic determination section (14), and a fine tuner (16) that is connected to the output side of the representative characteristic determination section (15).

6 Claims, 17 Drawing Sheets

FIG. 5

| Hearing ability class | representative characteristics |
|---|---|
| Hearing ability class 1 | adjustment 1A, adjustment 1B, adjustment 1C |
| Hearing ability class 2 | adjustment 2A, adjustment 2B, adjustment 2C, adjustment 2D |
| Hearing ability class 3 | adjustment 3A, adjustment 3B, adjustment 3C |
| Hearing ability class 4 | adjustment 4A, adjustment 4B |
| -------- | -------- | client class data storage section

110 client class data storage section

Hearing ability/class correspondence table

| 250 | 500 | 1k | 2k | 4k | class |
|---|---|---|---|---|---|
| 20dB | 20 | 20 | 20 | 20 | 1 |
| 20 | 20 | 20 | 20 | 21 | 1 |
| .. | .. | .. | .. | .. | .. |
| 30 | 30 | 30 | 30 | 30 | 2 |
| .. | .. | .. | .. | .. | .. |
| 60 | 60 | 60 | 60 | 58 | N-1 |
| 60 | 60 | 60 | 60 | 59 | N |
| 60 | 60 | 60 | 60 | 60 | N |

Class/representative characteristics correspondence table

| Hearing ability class | representative characteristics |
|---|---|
| Hearing ability class 1 | adjustment 1A, adjustment 1B, adjustment 1C |
| Hearing ability class 2 | adjustment 2A, adjustment 2B, adjustment 2C, adjustment 2D |
| Hearing ability class 3 | adjustment 3A, adjustment 3B, adjustment 3C |
| Hearing ability class 4 | adjustment 4A, adjustment 4B |
| ---- | ---- |
| Hearing ability class N | adjustment NA, adjustment NB, adjustment NC, adjustment ND |

FIG. 6

| Memory Number | Memory label | Adjustment Value Parameters |
|---|---|---|
| memory 68a | basic label 72a | 125 250 500 1K 2K 4K |
| memory 68b | television label 72e | 125 250 500 1K 2K 4K |
| memory 68c | music label 72f | 125 250 500 1K 2K 4K |
| memory 68d | train label 72c | 125 250 500 1K 2K 4K |

FIG. 12

| Memory No. / Environment | Level Range 1 | Level Range 2 | Level Range 3 | Level Range 4 | Level Range 5 | Level Range 6 |
|---|---|---|---|---|---|---|
| Basic label 72a (memory 68a) | 10% | 70% | 15% | 5% | 0% | 0% |
| Television label 72e (memory 68b) | 0% | 5% | 30% | 30% | 30% | 5% |
| Music label 72f (memory 68c) | 0% | 0% | 20% | 70% | 10% | 0% |
| Train label 72c (memory 68d) | 0% | 0% | 0% | 0% | 20% | 80% |

FIG. 15

HEARING AID FITTING DEVICE

This application is a Rule 1.53(b) Continuation of International Application No. PCT/W2011/002282, with the International Filing Date of Apr. 19, 2011.

TECHNICAL FIELD

The present invention relates to a hearing aid fitting device with which hearing aid usage setup is performed.

BACKGROUND ART

A hearing aid fitting device is used to set the aural characteristics of a hearing aid according to the hearing ability of the hearing aid user.

During actual setting, first the hearing ability of the user is measured from low to high tone in the audible frequency band, and the aural characteristics are adjusted on the basis of hearing ability data, which are the result of this measurement. However, this adjustment job often takes a long time even for a person with experience.

Specifically, the sense of hearing with respect to how sounds are heard varies greatly from one person to another, as well as with the measurement environment (the climate, size of the measurement space, and so forth), time, physical condition of the user, and so forth. Accordingly, even though the person doing the adjustment may be trying to proceed with the adjustment and gradually close in on the final value, the user will often say that a previous sound was better, forcing the adjustment work to go back, so the adjustment ends up taking a long time.

In view of this, an approach has been proposed with which the aural characteristics can be set in a shorter time by using an interactive genetic algorithm (see Patent Literature 1 below, for example).

CITATION LIST

Patent Literature

Patent Literature 1: Japanese Laid-Open Patent Application 2001-175637

SUMMARY

When an interactive genetic algorithm is used to set aural characteristics, a plurality of aural characteristics are readied according to the hearing ability of the hearing aid user, and the aural characteristics that are to be finally selected are picked out while comparing with these. Accordingly, the adjustment time may be shorter in some cases. Nevertheless, even when an interactive genetic algorithm is utilized, when aural characteristics are set one at a time, the adjusting technician has to spend the time doing adjustment work on the basis of interaction with the user, just as in the past, and as a result the adjustment may still end up taking a long time.

Also, despite the fact that the aural characteristics has been set as above, the user may not necessarily be satisfied when the device is used in the user's everyday life. More specifically, if there is a significant difference between the sound environment of the place where the hearing aid setting is performed, and the sound environment during actual use, the hearing aid user may be dissatisfied with the hearing aid during its actual use.

TECHNICAL PROBLEM

It is an object of the present invention to be able to perform hearing aid usage setup in a short time, and to improve the user's satisfaction with the hearing aid with respect to the setting of the hearing aid.

SOLUTION TO PROBLEM

The hearing aid fitting device of the present invention comprises a hearing ability input section, a representative characteristic determination section, an initial adjustment candidate selector, and a fine tuner. The hearing ability input section inputs hearing ability data for a user. The representative characteristic determination section extracts, as representative characteristics, representative hearing adjustment result data included in each cluster classified on the basis of the similarity of a plurality of hearing adjustment result data with respect to a plurality of hearing ability data similar to hearing ability data inputted from the hearing ability input section. The initial adjustment candidate selector switches while outputting as aural characteristics a plurality of hearing adjustment result data extracted as representative characteristics by the representative characteristic determination section, and makes the user select the one that is optimal for the user. The fine tuner fine tunes the hearing adjustment result data selected from the plurality of hearing adjustment result data switched by the initial adjustment candidate selector, for further compatibility with the user.

The hearing aid fitting device of the present invention comprises an input section to which hearing ability data for a user are inputted, a hearing aid reader that reads, from the hearing aid, usage environment log data for each of a plurality of types of usage environment and adjustment value parameters for each of the plurality of types of usage environment, a transmitter that transmits the hearing ability data, usage environment log data, and adjustment value parameters read by the hearing aid reader, an adjustment value parameter extractor that extracts a user close to the hearing ability data of the hearing aid user transmitted from the transmitter, extracts adjustment value parameters for each usage environment corresponding to a plurality of usage environments set by the hearing aid user from among the plurality of usage environments set by the extracted user, and extracts and transmits adjustment value parameters for each usage environment close to the usage environment log data of the hearing aid user from the extracted adjustment value parameters for each of the extracted usage environments, a receiver that receives adjustment value parameters for each of the plurality of types of usage environment extracted and transmitted by the adjustment value parameter extractor, and a hearing aid writer that writes the adjustment value parameters to an adjustment value data storage section of the hearing aid.

ADVANTAGEOUS EFFECTS

With the hearing aid fitting device of the present invention, the adjusting technician merely inputs hearing ability data through a hearing ability input section, the result being that hearing adjustment result data are outputted with respect to a plurality of hearing ability data similar to these hearing ability data. These hearing adjustment result data take into account the preferences of many people having that hearing ability, so there is no need to produce the characteristics to be selected as in the past. As a result, the usage setup for the hearing aid can be performed in a short time. Also, the selected hearing adjustment result data are fine tuned by the fine tuner, so the result is aural characteristics that are matched to the user, so the hearing aid is comfortable to use and provides a good improvement in hearing.

BRIEF DESCRIPTION OF DRAWINGS

FIG. 5 is a hearing ability/class correspondence table and a class/representative characteristic correspondence table stored in a client class data storage section of the hearing aid fitting device in FIG. 1;

FIG. 6 is a diagram of a table stored in the client class data storage section of the hearing aid fitting device in FIG. 1;

FIG. 12 is a diagram of a hearing aid value data storage section of the hearing aid in the hearing aid fitting system in FIG. 8;

FIG. 15 is a diagram of the operating state of the hearing aid fitting system in FIG. 8;

DESCRIPTION OF EMBODIMENTS

Embodiment 1

An embodiment of the present invention will now be described through reference to the appended drawings.

Figure 1:
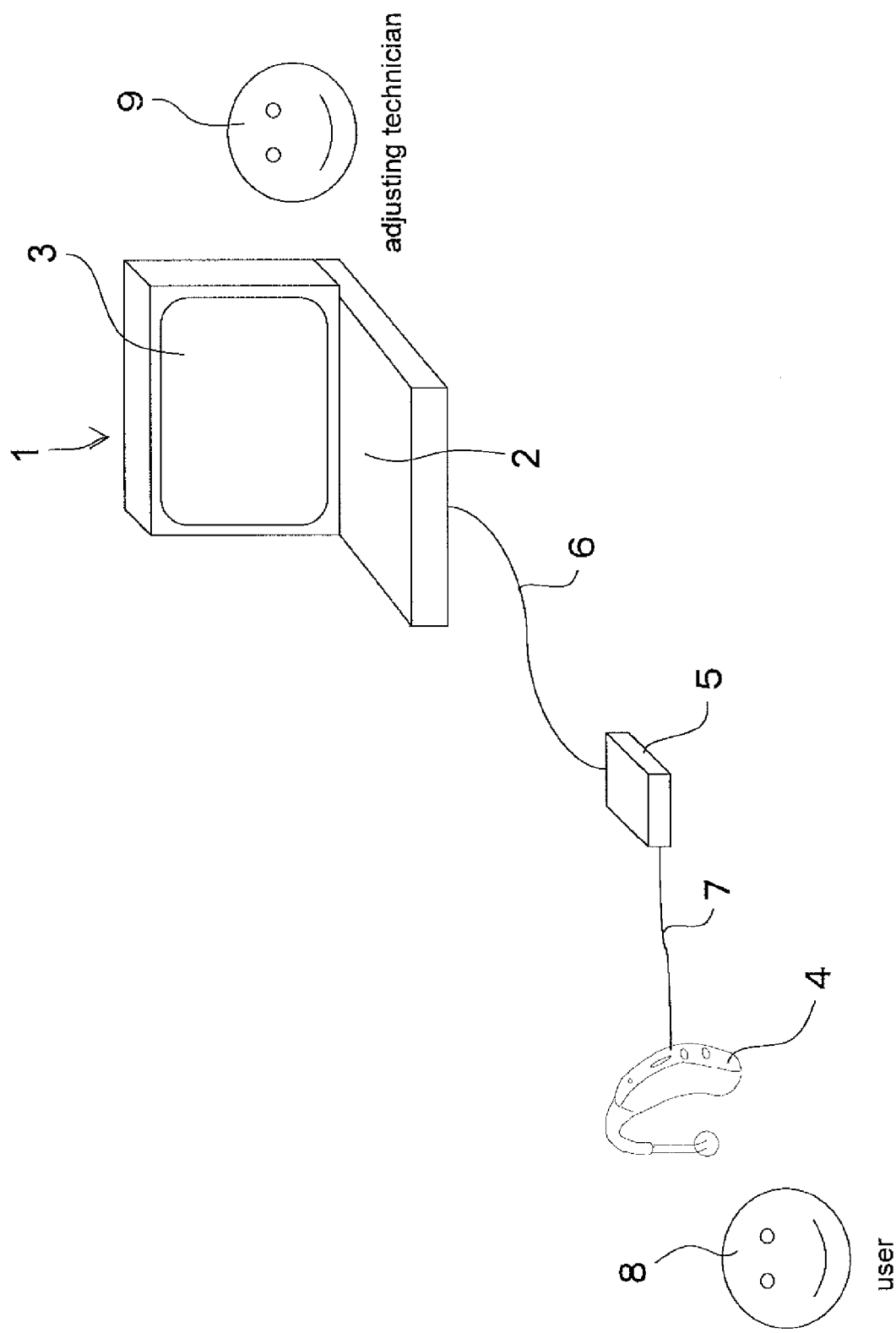
FIG. 1 is a schematic illustrating the hearing aid fitting device pertaining to an embodiment of the present invention.

As shown in FIG. 1, the hearing aid fitting device 1 of this embodiment comprises an input section 2 and a display section 3 on its surface. The hearing aid fitting device 1 and a hearing aid 4 are connected to each other via a connector box 5 and wires 6 and 7. Two of the hearing aids 4 are readied, one each for the left and right ears of a user 8, but just the right one is shown in FIG. 1 to simplify the description.

An adjusting technician 9 operates the hearing aid fitting device 1 to perform usage setup for the hearing aid 4.

Figure 2:
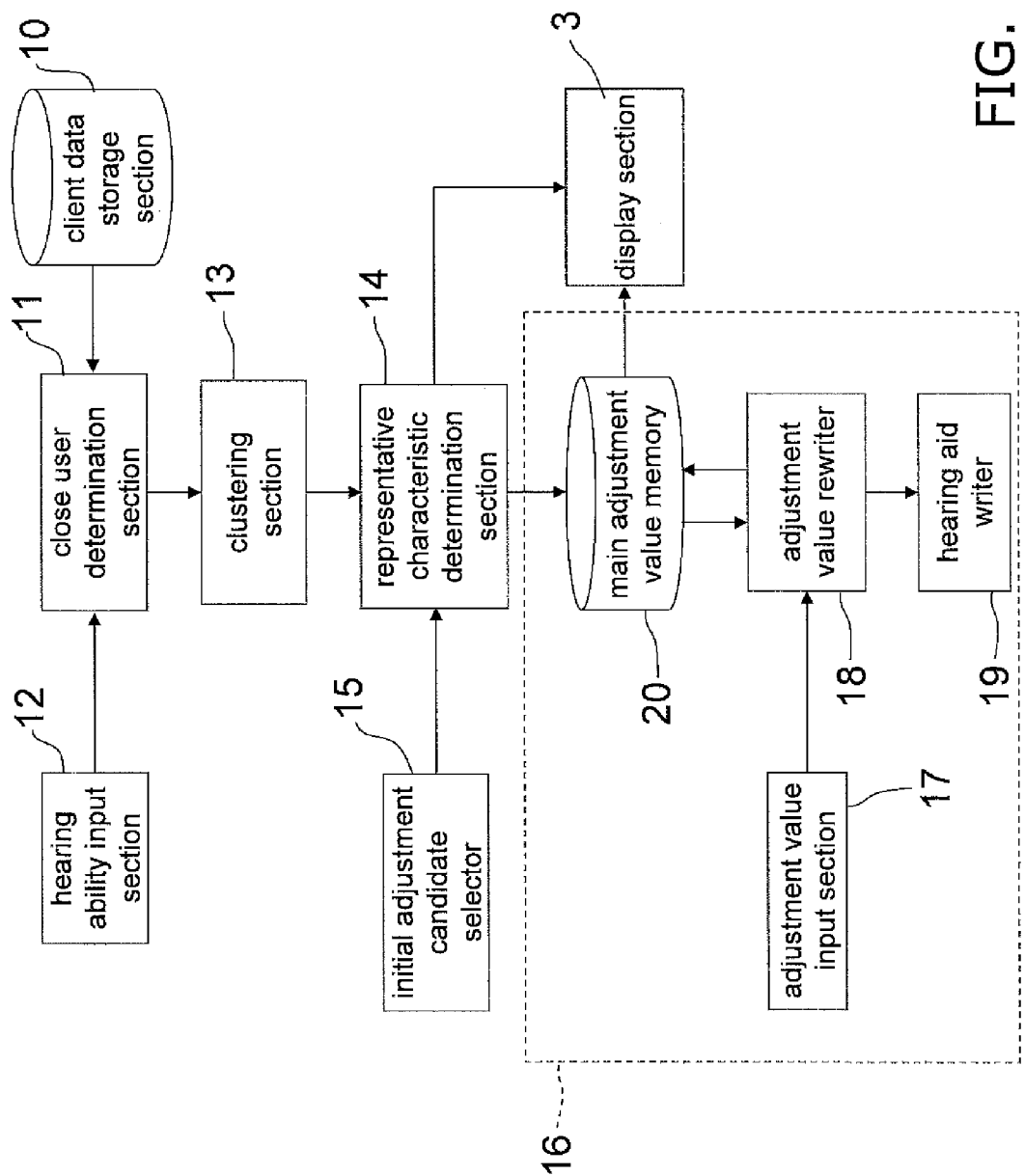
FIG. 2 is a control block diagram of the hearing aid fitting device in FIG. 1.

FIG. 2 shows control blocks for the hearing aid fitting device 1.

The hearing aid fitting device 1 comprises a client data storage section 10, a close user determination section 11, a hearing ability input section 12, a clustering section 13, a representative characteristic determination section 14, an initial adjustment candidate selector 15, a fine tuner 16, and the display section 3.

A plurality of hearing ability data acquired in the course of performing setup of the hearing aid 4 for many clients in the past, and hearing adjustment result data corresponding to the plurality of hearing ability data are stored in the client data storage section 10. That is, other users in the past also always had their hearing ability measured first in the course of performing usage setup of the hearing aid 4, after which adjustment was performed to set the final aural characteristics. Accordingly, hearing ability data obtained by hearing ability measurement and hearing adjustment result data that are the final aural characteristics corresponding to these hearing ability data are associated with each other and stored in the client data storage section 10 as a set.

Also, the client data storage section 10 is connected to the input side of the close user determination section 11. Furthermore, the hearing ability input section 12 is connected to the other input side of the close user determination section 11.

The hearing ability data inputted to the hearing ability input section 12 is obtained as the result of measuring the hearing ability of the user from low to high tone in the audible frequency band in a quiet measurement space.

The clustering section 13 is connected to the output side of the close user determination section 11. Further, the representative characteristic determination section 14 is connected to the output side of the clustering section 13. Also, the initial adjustment candidate selector 15 is connected to the input side of the representative characteristic determination section 14. Further, the display section 3 and the fine tuner 16 are connected to the output side of the representative characteristic determination section 14.

The fine tuner 16 comprises an adjustment value input section 17 provided to the input section 2 (see FIG. 1), an adjustment value rewriter 18 to which the adjustment value is inputted from the adjustment value input section 17, a hearing aid writer 19 connected to the output side of the adjustment value rewriter 18, and a main adjustment value memory 20 connected to the representative characteristic determination section 14, the adjustment value rewriter 18, and the display section 3. The hearing ability input section 12 and the adjustment value input section 17 are included in the input section 2 (see FIG. 1).

Next, a hearing aid fitting method will be described through reference to FIGS. 2 and 3.

Figure 3:
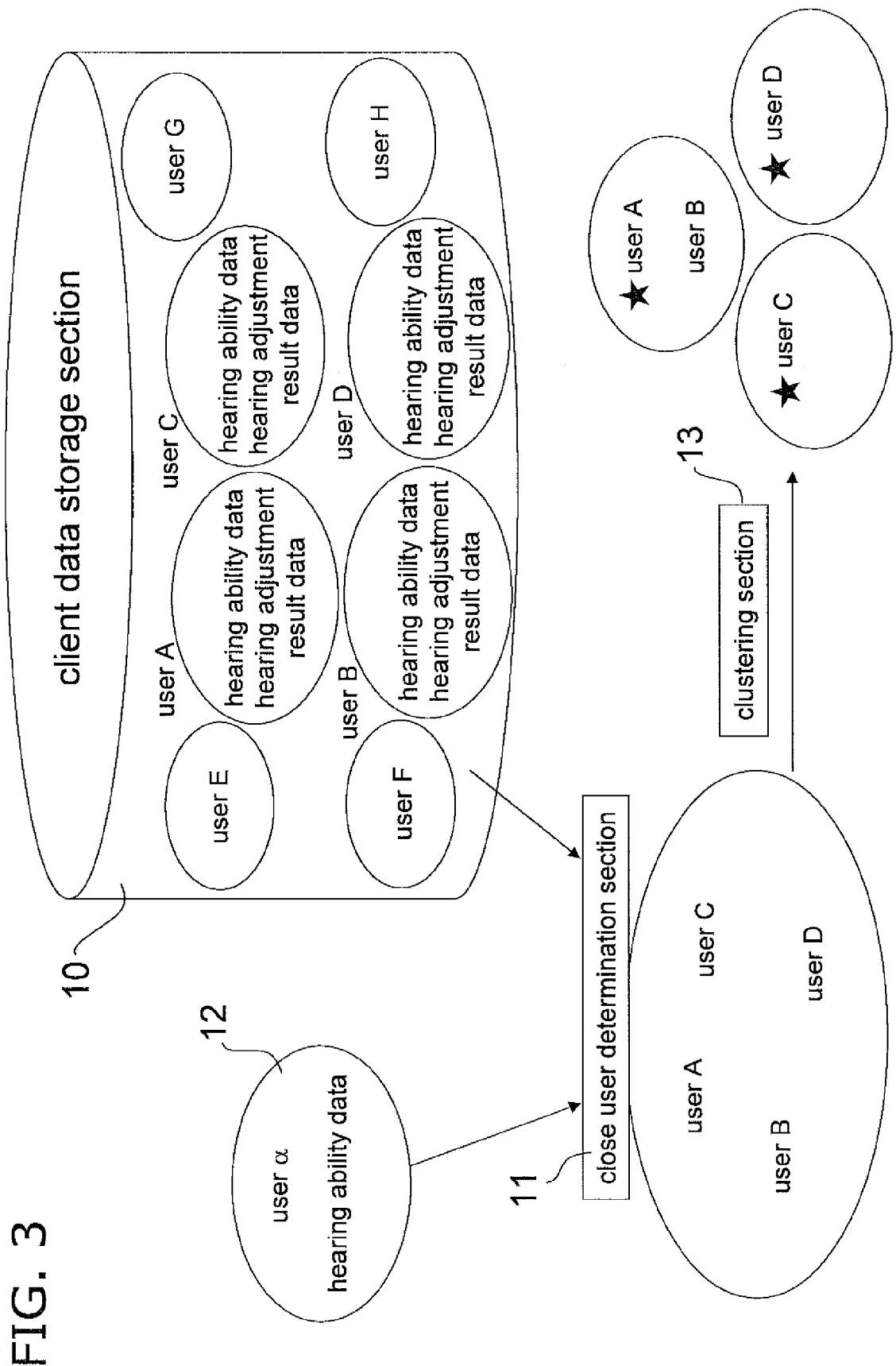
FIG. 3 is a diagram illustrating a hearing aid fitting method using the hearing aid fitting device in FIG. 1.

First, as shown in FIGS. 2 and 3, hearing ability data about the user 8 are inputted from the hearing ability input section 12. Then, at the close user determination section 11, hearing adjustment result data with respect to a plurality of hearing ability data similar to the hearing ability data inputted from the hearing ability input section 12 are specified and pulled out of the client data storage section 10.

More precisely, as discussed above, hearing ability data obtained by hearing ability measurement and acquired in the course of performing usage setup of the hearing aids 4 of other users in the past, and hearing adjustment result data that are the final aural characteristics corresponding to these hearing ability data are stored in the client data storage section 10 in a state of being associated with each other. For example, as shown in FIG. 3, hearing ability data obtained ahead of time by hearing ability measurement for user A, user B, user C, user D, user E, user F, user G, and user H, and hearing adjustment result data that are final aural characteristics with respect to the these hearing ability data are stored as sets in the client data storage section 10.

Next, when the hearing ability data for user α, who is the user 8 of the hearing aid to be adjusted now, is inputted to the hearing ability input section 12, hearing adjustment result data corresponding to a plurality of hearing ability data (user A, user B, user C, and user D) similar to the hearing ability data of user α inputted from the hearing ability input section 12 are specified and pulled out of the client data storage section 10 at the close user determination section 11. At this point, whether or not the hearing ability data of user α (the user 8) is similar to the hearing ability data of user A, etc., can be determined as follows, for example.

The audible levels at a plurality of frequencies over the measurement frequency range for the hearing ability data of each person are recorded, and these hearing ability data are recognized as a single line. Since the hearing aid data can be recognized as a single line, the hearing ability data for user A, user B, user C, and user D similar to the hearing ability data of user α can be picked out by comparing the shape of the lines (the height, slope, etc.). Thus, hearing adjustment result data that are the final aural characteristics for user A, user B, user C, and user D can be pulled out to the close user determination section 11. As for the method for specifying the close users here, a vector display of the client hearing ability data may be made, and the close users may be specified on the basis of the distance between vectors.

Next, the plurality of hearing adjustment result data pulled out by the close user determination section 11 are clustered. The term clustering here refers to classifying a plurality of hearing adjustment result data on the basis of similarity. This clustering can be performed on the basis of the distance between vectors in a vector display of client hearing adjustment result data. More specifically, a known k-means method can be used, for example.

For instance, if the hearing adjustment result data that are the final aural characteristics for user A and user B are extremely similar to one another, the clustering section 13 classifies the hearing adjustment result data for user A and user B into the same cluster. As a result, the clustering section 13 classifies into three clusters, namely, a first cluster including the hearing adjustment result data for user A and user B, a second cluster including the hearing adjustment result data for user C, and a third cluster including the hearing adjustment result data for user D.

Next, the representative characteristic determination section 14 extracts representative characteristics from each of the clusters.

In this embodiment, the representative characteristic determination section 14 extracts as representative characteristics, for example, the hearing adjustment result data for user A from the first cluster, that for user C from the second cluster, and that for user D from the third cluster, and these are outputted to the display section 3.

Here, a method in which the user closest to the mean or centroid of each cluster is selected for the representative characteristics can be used in specifying the representative characteristics. Alternatively, the centroid data for all of the data included in the various clusters can be used for the representative characteristics. Alternatively, the mean value data for all of the data included in the various clusters can be used for the representative characteristics.

When hearing adjustment result data for the user closest to the mean or centroid are used for the representative characteristics, comments and so forth made when that user had adjustments made can be referred to, so more specific information relating to adjustment can be obtained. Also, when an estimated value in the form of a mean or centroid of the various clusters is used for the representative characteristics, and particularly when the data in a cluster are small in quantity and highly dispersed, characteristics can be expressed that are closer to the representative characteristics of that cluster than when the user closest to the mean or centroid is used directly for the representative characteristics. Thus, the differences between representative characteristics can be made clearer.

Figure 4:
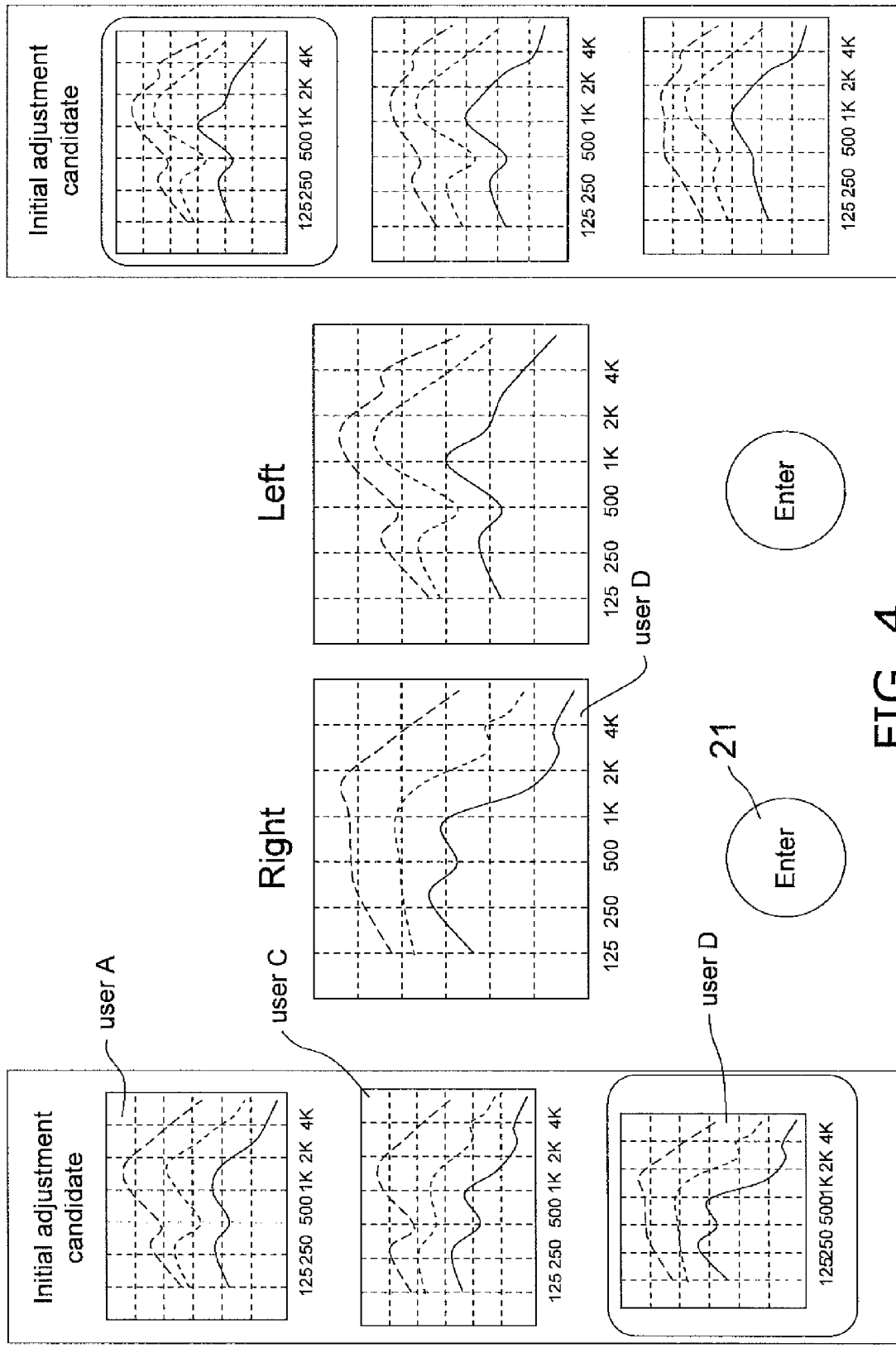
FIG. 4 is a diagram illustrating a hearing aid fitting method using the hearing aid fitting device in FIG. 1.

FIG. 4 shows what is displayed on the display section 3, and shows the display of the hearing adjustment result data that are the final aural characteristics for user A, user C, and user D. In FIG. 4, only the usage setup for the right hearing aid 4 of user α (the user 8) is explained as follows, but in actual practice, once the usage setup for the right hearing aid has been finished, the usage setup of the left hearing aid is then performed.

Next, the hearing adjustment result data that are the final aural characteristics for user A, user C, and user D are switched as the aural characteristics by the initial adjustment candidate selector 15 while user α undergoes a hearing test. After user α has listened to all of these, and has selected as the initial adjustment candidate the hearing adjustment result data for user D as the best match, for example, the hearing adjustment result data for user D are displayed on the display section 3 as shown in FIG. 4.

The hearing adjustment result data for user D are sent through the main adjustment value memory 20 to the adjustment value rewriter 18.

Next, the hearing adjustment result data for user D are fined tuned by the adjustment value input section 17. Specifically, the hearing adjustment result data for user D for the initial adjustment candidate are corrected so as to make the sound easier for user α to hear. The fine-tuned hearing adjustment result data for user D are displayed on the display section 3.

It is preferable here if the hearing adjustment result data for user D prior to fine tuning and the hearing adjustment result data for user D after fine tuning are displayed side by side. More specifically, first two sets of the hearing adjustment result data for user D prior to fine tuning are displayed side by side for the right ear. Then, when fine tuning is finished, one of the two displays is changed to the hearing adjustment result data for user D that have been fine tuned. The other display remains as the hearing adjustment result data for user D. The same applies to the hearing aid for the left ear.

Consequently, the adjusting technician 9 or user α can seen the hearing adjustment result data before and after fine tuning at a glance, which makes the difference between the two easy to recognize visually.

When this fine tuning is finished, an enter button 21 is pressed by the adjusting technician 9. The hearing aid writer 19 then rewrites the aural characteristics of the hearing aid 4, and the usage setup is complete. Also, the hearing ability data for user α and the hearing adjustment result data that are the final aural characteristics are associated with each other and stored in the client data storage section 10 as a set.

As discussed above, with this embodiment, merely by inputting the hearing ability data for user α from the hearing ability input section 12, it is possible for the hearing adjustment result data with respect to a plurality of hearing ability data similar to this hearing ability data to be pulled out from the client data storage section 10 to the close user determination section 11. A plurality of data not mutually similar are selected and outputted, so that these hearing adjustment result data take into account the preferences of many people having that hearing ability, so there is no need to produce the characteristics to be selected as in the past. As a result, the usage setup for the hearing aid 4 can be performed in a short time.

Furthermore, the various hearing adjustment result data are classified by similarity, and representative hearing adjustment result data are extracted and outputted from each cluster, so repeatedly outputting similar hearing adjustment result data classified into the same cluster can be avoided. As a result, the fitting of the hearing aid can be carried out more efficiently than in the past.

Also, the selected hearing adjustment result data are fine tuned by the fine tuner 16, so the result is aural characteristics that are matched to the user 8 (user α), and the hearing improvement and usage feel to the user 8 can be improved.

In the above embodiment, an example was described in which the hearing aid fitting device 1 and the hearing aid 4 were connected by the wires 6 and 7, but the present invention is not limited to or by this example.

For instance, the hearing aid fitting device 1 and the hearing aid 4 may be connected wirelessly.

Also, the hearing aid fitting method pertaining to the above embodiment may at least partially be carried out by having a computer execute a program. This program can be delivered via a CD-ROM or other such recording medium, or via the Internet or another such transmission medium.

Embodiment 2

The hearing aid fitting device pertaining to another embodiment of the present invention will now be described through reference to the drawings.

In Embodiment 1 above, after the hearing ability of the user 8 was inputted, close users with similar hearing ability levels were extracted from the client data storage section 10, and clustering was performed on the basis of the adjustment results for the extracted closer users. However, this clustering processing takes up considerable computation time.

In view of this, with the hearing aid fitting device in this embodiment, hearing ability patterns are classified ahead of time into a plurality of classes (hereinafter referred to as hearing ability classes), and a plurality of representative characteristics corresponding to each of the hearing ability classes are readied.

Consequently, aural characteristics that take into account the various preferences had by users with the same hearing ability can be evaluated simply by searching for representative characteristics on the basis of the hearing ability level had by the user for whom adjustment is to be performed.

In this embodiment, a database that holds a plurality of representative characteristics corresponding to each of the hearing ability classes is called a client class database.

A client class database can be produced ahead of time on the basis of the data in a client data storage section that holds a large quantity of client data having various hearing ability patterns.

For example, hearing ability data can be expressed as vectors and clustered using a method such as k-means. The adjustment results for the clients belonging to each of the classes obtained by this clustering may be clustered again using k-means or another such method, and the representative characteristics then extracted.

FIG. 5 shows an example of a client class data storage section 110.

A hearing ability class indicates a cluster of hearing abilities classified ahead of time by k-means or another such method. The representative characteristics are found by utilizing k-means or another such method for that entire class. A hearing ability graph given for each of the hearing ability classes shows the centroid, mean value, etc., for that class.

As shown in FIG. 5, when the client class data storage section 110 is used, it can be determined to which hearing ability class the hearing ability of the user to undergo new adjustment belongs by specifying the class closest to the hearing ability of that user, and the representative characteristics stored in that class can be specified.

Also, a hearing ability class may be produced ahead of time on the basis of the pattern of hearing abilities, such as abrupt high-tone hearing loss or gradual sloping high-tone hearing loss. Specifically, classes can be defined ahead of time for all hearing ability classes, etc., so that the class to which belongs the hearing aid user for whom adjustment is to be performed can be specified.

More specifically, as shown in FIG. 6, a hearing ability/class correspondence table and a class/representative characteristic correspondence table are readied in the client class data storage section 110, and the hearing ability/class correspondence table is searched to find which class the hearing ability of the user of the hearing aid to be adjusted belongs to. The representative characteristics corresponding to the class that is searched for may be searched for in the class/representative characteristic correspondence table.

Figure 7:
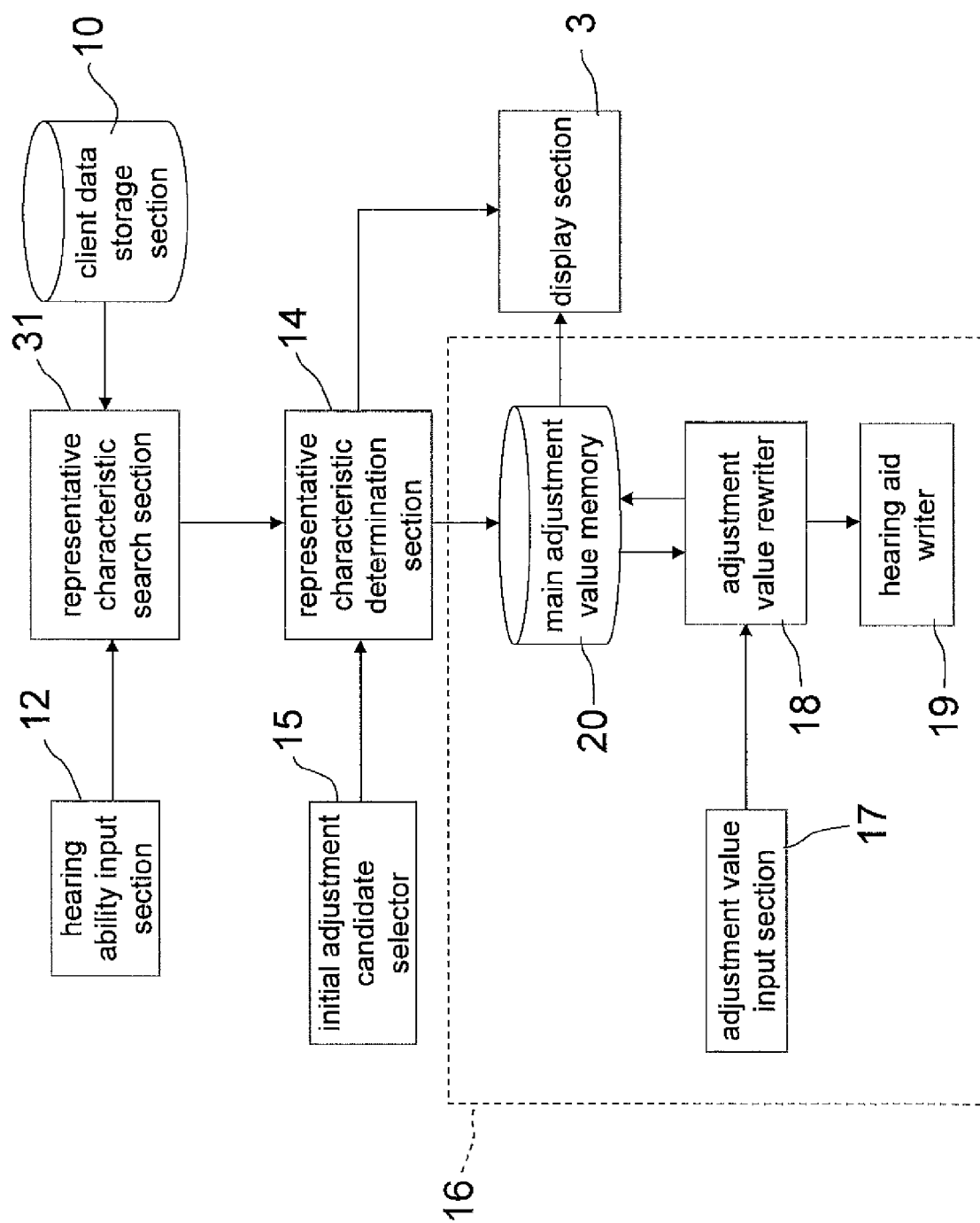
FIG. 7 is a control block diagram of the hearing aid fitting device in FIG. 1.

FIG. 7 shows the block configuration expressing the above hearing aid fitting method.

The hearing aid fitting device of this embodiment comprises a representative characteristic search section 31 in place of the close user determination section 11 and the clustering section 13 in FIG. 2.

The representative characteristic search section 31 specifies the hearing ability class for the hearing aid user, and searches for the representative characteristics, by using client data stored in the client data storage section 10 on the basis of the hearing ability level of the hearing aid user inputted to the hearing ability input section 12.

With the above constitution, hearing ability classes and representative characteristics corresponding to the various hearing ability classes are readied in advance, which allows the same effect to be obtained as that obtained with Embodiment 1 above, but without having to perform clustering of the hearing adjustment result data each time.

Consequently, since there is no need to perform time-consuming clustering processing, the hearing aid can be set up more efficiently so that the aural characteristics are suited to the user.

Furthermore, since the various hearing adjustment result data are pre-classified on the basis of similarity, and one set of representative hearing adjustment result data is extracted and outputted from each class, repeatedly outputting similar hearing adjustment result data classified into the same cluster can be avoided. As a result, the fitting of the hearing aid can be carried out more efficiently than in the past.

The constitution of this embodiment is particularly effective in environments and systems in which the client class data storage section 110 is on a network and the client class data storage section 110 can be referred to through the Web from a retailer anywhere in the world.

Embodiment 3

The hearing aid fitting device pertaining to yet another embodiment of the present invention will now be described through reference to the drawings.

In Embodiments 1 and 2 above, as shown in FIG. 4, the constitution was such that the representative characteristics were displayed on the screen of the hearing aid fitting device, allowing them to be listened to an compared, but the method for presenting the representative characteristics to the adjusting technician is not limited to the method shown in this drawing, and may instead be any expression method as long as the nature of the representative characteristics can be conveyed.

For example, as shown in FIG. 4, when three representative characteristics are obtained, the user may be given announcements of "This is the first candidate," "This is the second candidate," and "This is the third candidate," whereupon each of the characteristics is written to the hearing aid, a listening test is conducted for the sounds processed on the basis of the aural characteristics, and the user listens to and compares the sounds.

Also, verbal expressions of the features of each of the representative characteristics may be stored as additional information, these words may be displayed on the screen instead of a graph, and the characteristics to be written to the hearing aid may be selected from these.

Embodiment 4

The hearing aid fitting device pertaining to an embodiment of the present invention will now be described through reference to the appended drawings.

Figure 8:
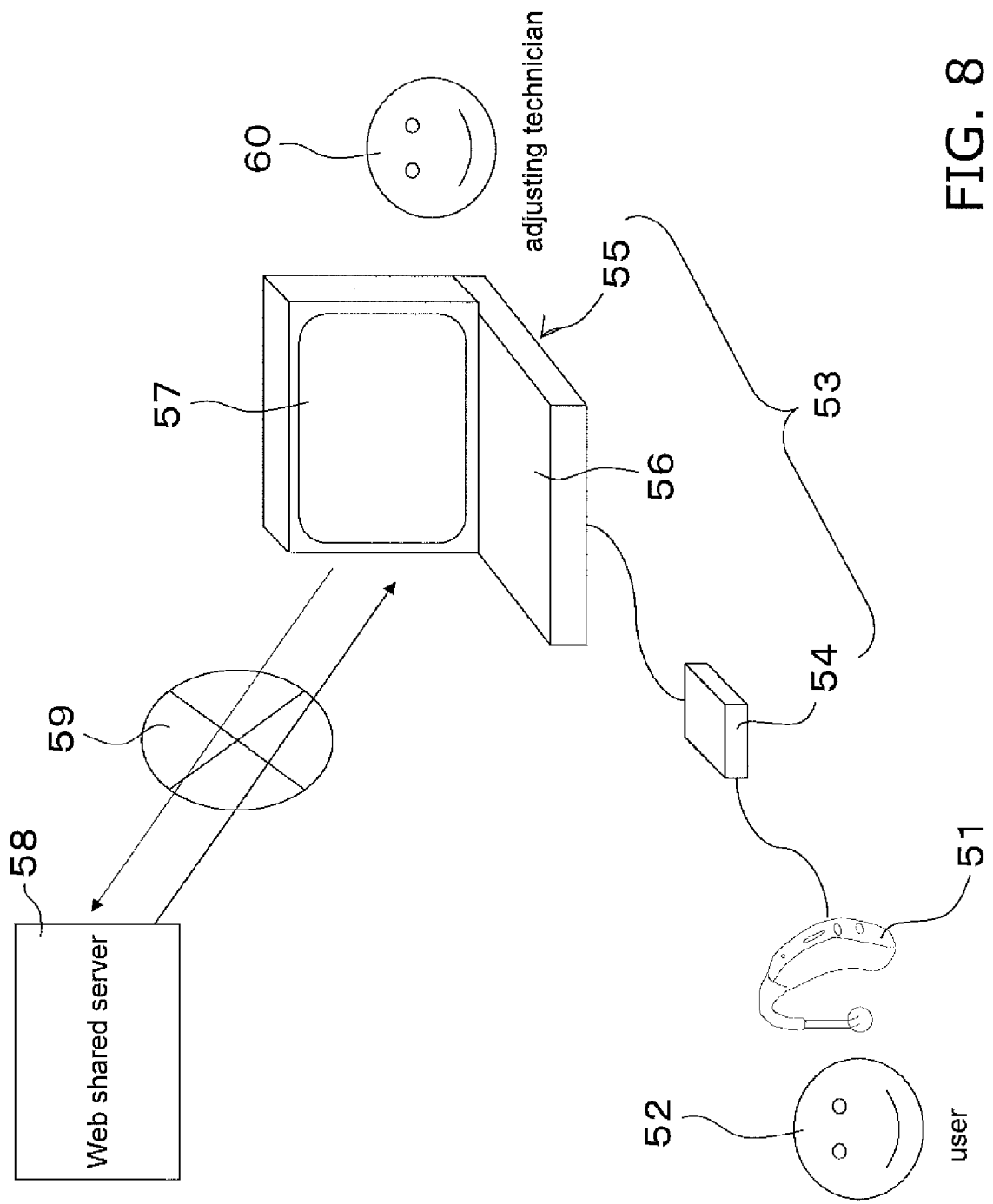
FIG. 8 is a schematic diagram illustrating a hearing aid fitting system, and a fitting method in which this system is used, pertaining to an embodiment of the present invention.

In FIG. 8, 51 is a hearing aid, and a user 52 has the hearing aid 51 mounted on both the left and right ears, but in FIG. 8 just one of these is connected. FIG. 8 shows a state in which the hearing aid 51 is connected to a fitting device 53 and fitting is performed.

As shown in FIG. 8, the hearing aid fitting system of this embodiment comprises the fitting device 53 to which the hearing aid 51 is connected, and a Web shared server 58.

As shown in FIG. 8, the fitting device 53 has a fitting PC 55 and a connector box 54. The connector box 54 connects the hearing aid 51 and the fitting PC 55. The fitting device 53 is operated by the adjusting technician 60 who performs the fitting.

As shown in FIG. 8, the fitting PC 55 comprises an input section 56 and a display section 57. Further, the fitting PC 55 is connected to the Web shared server 58 via a network 59.

Figure 9:
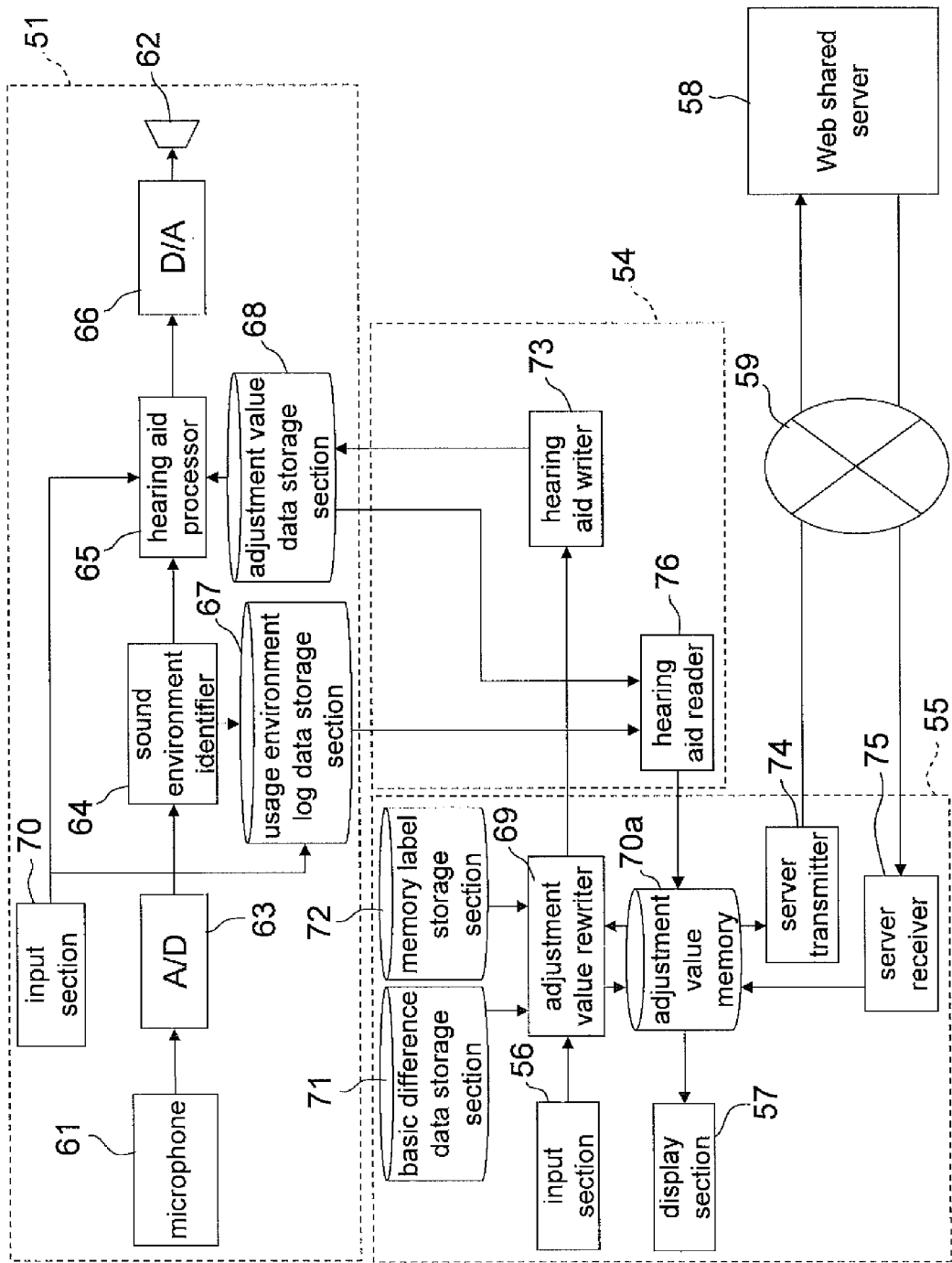
FIG. 9 is a control block diagram of the hearing aid fitting device in FIG. 8.

As shown in FIG. 9, the hearing aid 51 has connected to it an A/D converter 63, a sound environment identifier 64, a hearing aid processor 65, and a D/A converter 66, in that order from a microphone 61 toward a receiver (speaker) 62. A usage environment log data storage section 67 is connected to the sound environment identifier 64. An adjustment value data storage section 68 is connected to the hearing aid processor 65. An input section 70 is connected to the hearing aid processor 65 and the usage environment log data storage section 67.

As discussed above, the fitting PC 55 has connected to it the input section 56 and the display section 57. Of these, the input section 56 is connected to an adjustment value rewriter 69. The display section 57 is connected to an adjustment value memory 70a. The adjustment value rewriter 69 is connected to a basic difference data storage section 71, a memory label storage section 72, and a hearing aid writer 73 inside the connector box 54.

To the adjustment value memory 70a are connected a server transmitter 74, a server receiver 75, and a hearing aid reader 76. The server transmitter 74 sends to the Web shared server 58 adjustment value parameters, usage environment log data, and hearing ability data about the user 52 who uses the hearing aid 51. The server receiver 75 receives adjustment value parameters for each of a plurality of types of usage environment sent back from the Web shared server 58. The hearing aid reader 76 reads usage environment log data and adjustment value parameters from the hearing aid 51.

Figure 10:
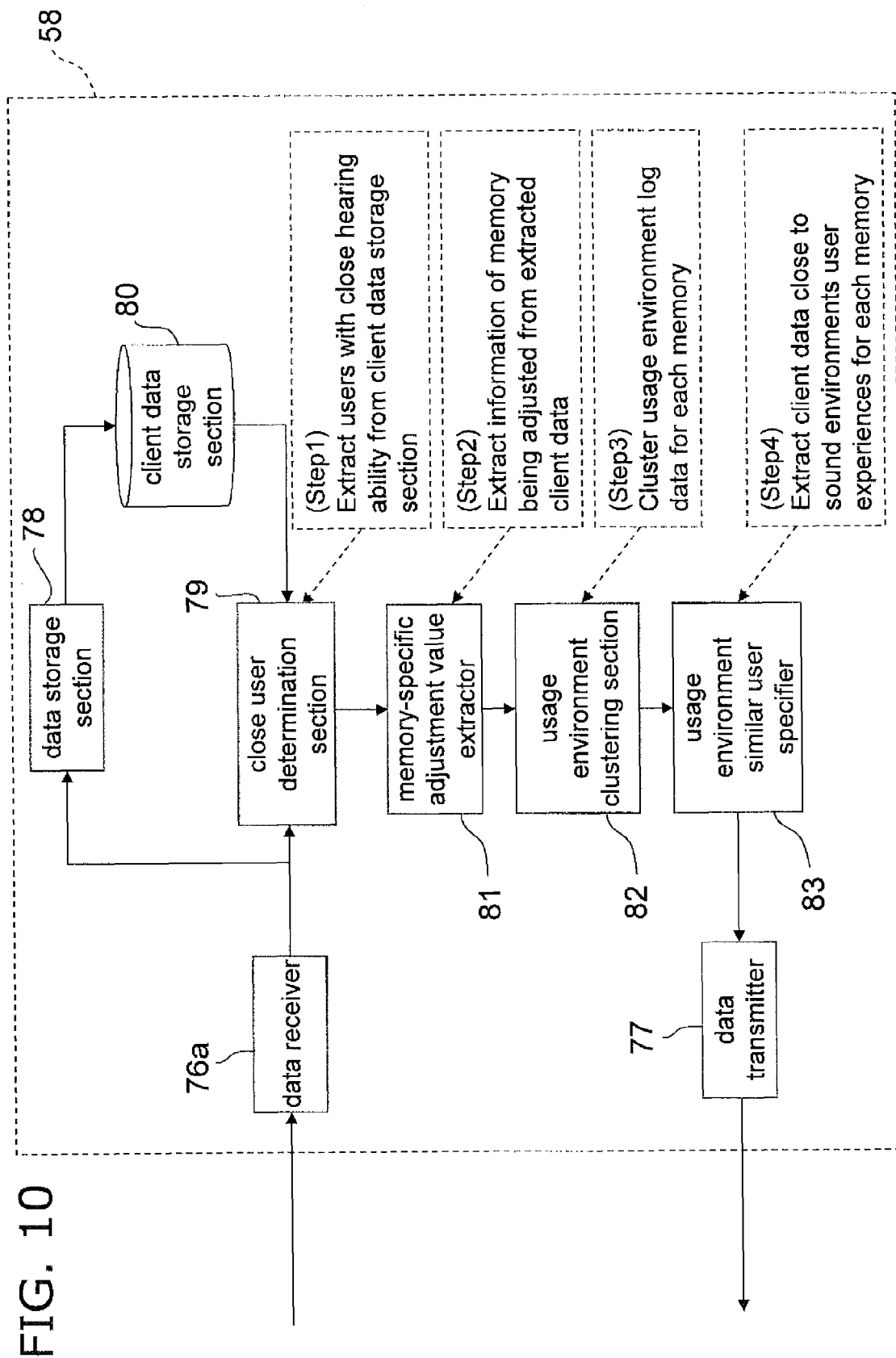
FIG. 10 is a control block diagram of the hearing aid fitting device in FIG. 8.

Meanwhile, as shown in FIG. 10, the Web shared server 58 has a data receiver 76a and a data transmitter 77. The data receiver 76a receives adjustment value parameters, usage environment log data, and hearing ability data about the user 52 sent from the server transmitter 74. The data transmitter 77 sends adjustment value parameters for each of a plurality of types of usage environment to the server receiver 75.

A data storage section 78 and a close user determination section 79 are connected to each other in series on the output side of the data receiver 76a. A client data storage section 80 is connected on the output side of the data storage section 78. The close user determination section 79 is connected on the output side of the client data storage section 80. A memory-specific adjustment value extractor 81, a usage environment clustering section 82, and a usage environment similar user specifier 83 are connected in that order between the output side of the close user determination section 79 and the input side of the data transmitter 77.

Figure 11:
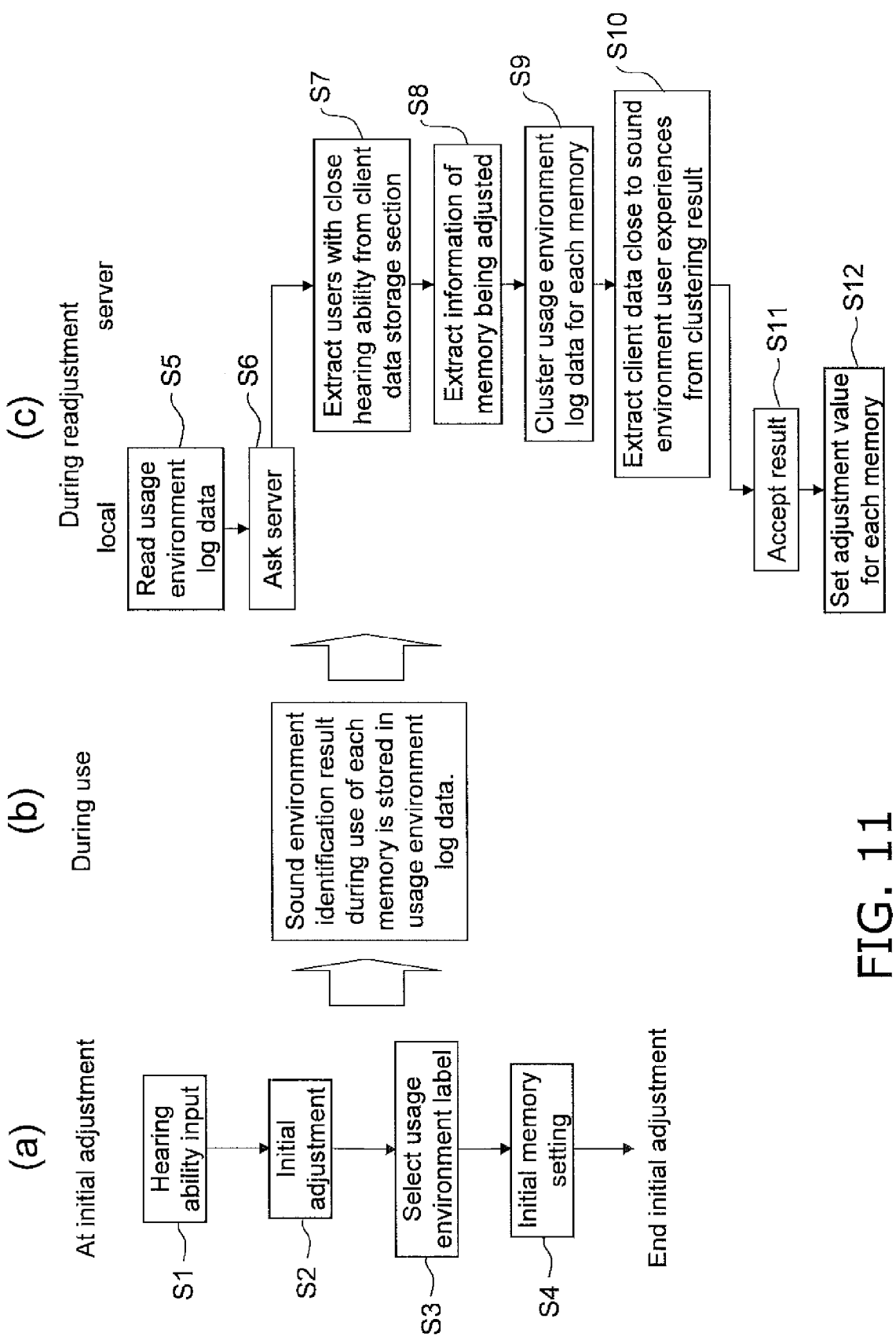
FIGS. 11a, 11b, and 11c are flowcharts showing the flow of operation in the hearing aid fitting system in FIG. 8.

With the hearing aid fitting system of this embodiment, in the constitution described above, the first fitting of the hearing aid 51 is carried out according to the flow shown in FIG. 11a, by a known method.

Specifically, first the hearing ability data separately measured for the user 52 is inputted (S1 in FIG. 11a) to the input section 56 in FIG. 9.

Next, the user 52 listens to sounds at specific frequency intervals while initial adjustment is performed by a known method (S2 in FIG. 11a).

Next, four (for example) usage environment labels are selected from the memory label storage section 72, according to what the user 52 wants (S3 in FIG. 11a).

Here, the usage environment label is the classification name for the environments in which it is expected that the user 52 will want to use the hearing aid, and the adjustment value parameters vary from one environment to the next. In this embodiment, different environments are set in memories 68a, 68b, 68c, and 68d.

Examples of the "environments in which it is expected that the user 52 will want to use the hearing aid" include an ordinary environment, a noisy environment, an environment of riding on a train, an environment of being at a party, an environment of watching television, an environment of listening to music, an environment of being in a quiet place, and so forth. The usage environment label corresponding to an ordinary environment is a basic label. The usage environment label corresponding to a noisy environment is a noisy use label. The usage environment label corresponding to an environment of riding on a train is a train label. The usage environment label corresponding to an environment of being at a party is a party label. The usage environment label corresponding to an environment of watching television is a television label. The usage environment label corresponding to an environment of listening to music is a music label. And the usage environment label corresponding to an environment of being in a quiet place is a quiet place label.

Figure 13:
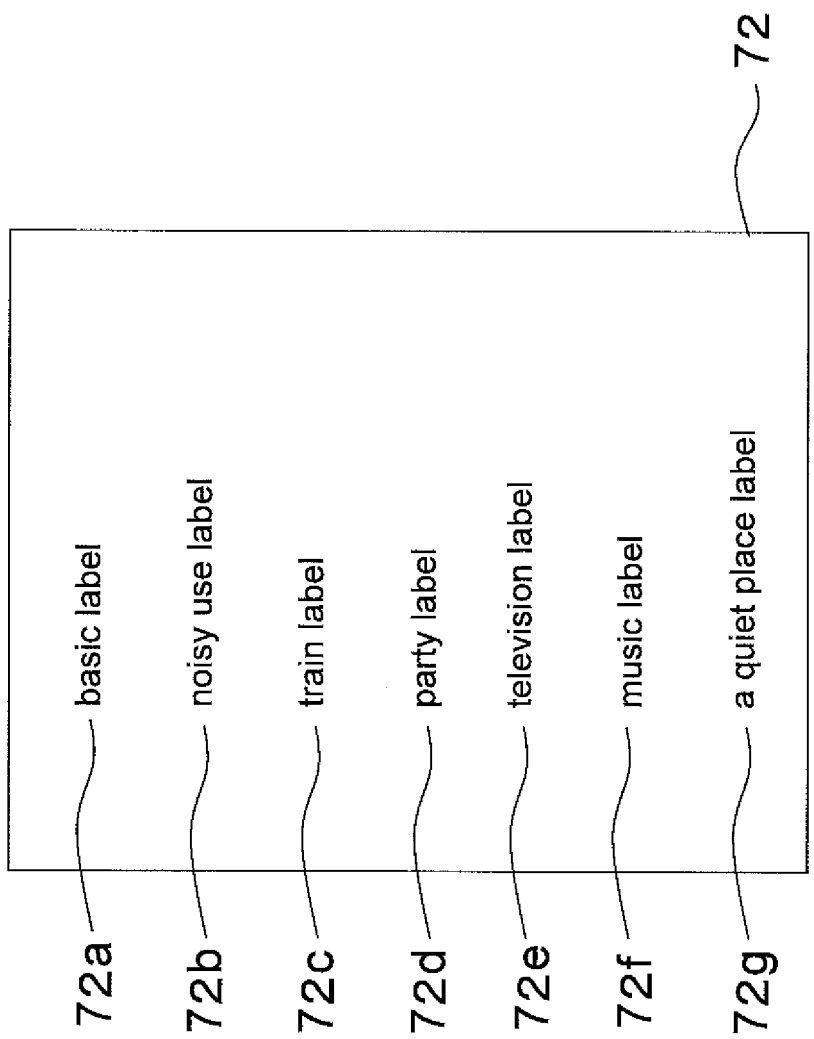
FIG. 13 is a diagram of a hearing aid value data storage section of the hearing aid in the hearing aid fitting system in FIG. 8.

More specifically, as shown in FIG. 13, a basic label 72a, a noisy use label 72b, a train label 72c, a party label 72d, a television label 72e, a music label 72f, and a quiet place label 72g are readied inside the memory label storage section 72, and four usage environment labels are selected from among these.

In this embodiment, as shown in FIG. 12, the four memories 68a, 68b, 68c, and 68d are readied in the adjustment value data storage section 68 of the hearing aid 51. The basic label 72a for electrical identification is affixed to the memory 68a. The television label 72e for electrical identification is affixed to the memory 68b. The music label 72f for electrical identification is affixed to the memory 68c. The train label 72c for electrical identification is affixed to the memory 68d.

At this point, adjustment value parameters for the above-mentioned initial adjustment are inputted to the memory 68a to which the basic label 72a is affixed. Also, since the adjustment value parameters for this initial adjustment are basic, the differences with respect to the adjustment value parameters for the noisy use label 72b, the train label 72c, the party label 72d, the television label 72e, the music label 72f, and the quiet place label 72g are stored in the above-mentioned basic difference data storage section 71.

Therefore, as discussed above, when the television label 72e, the music label 72f, and the train label 72c are selected, as shown in FIG. 12, adjustment value parameters with respect to the television label 72e, the music label 72f, and the train label 72c are formed by the adjustment value rewriter 69 (see FIG. 9).

The adjustment value parameters for the basic label 72a, the television label 72e, the music label 72f, and the train label 72c shown in FIG. 12 and thus formed are written to the four memories 68a, 68b, 68c, and 68d of the adjustment value data storage section 68 via the hearing aid writer 73 (S4 in FIG. 11a).

The user 52 goes about his everyday life using the hearing aid 51, which operates on the basis of the adjustment value parameters set as above. That is, in a normal state, the user 52 selects a state in which hearing aid processing is handled with the adjustment value parameters of the memory 68a in the hearing aid processor 65, via the input section 70 of the hearing aid 51. When watching television, the user selects a state in which hearing aid processing is handled with the adjustment value parameters of the memory 68b in the hearing aid processor 65 via the input section 70 of the hearing aid 51. When listening to music, the user selects a state in which hearing aid processing is handled with the adjustment value parameters of the memory 68c in the hearing aid processor 65 via the input section 70 of the hearing aid 51. When riding a train, the user selects a state in which hearing aid processing is handled with the adjustment value parameters of the memory 68d in the hearing aid processor 65 via the input section 70 of the hearing aid 51.

As discussed above, when the memories 68a to 68d are selected according to the usage environment via the input section 70 of the hearing aid 51, the sound environment identifier 64 decides on the sound pressure level once every four seconds. As a result, as shown in FIG. 15, usage environment log data are recorded to the usage environment log data storage section 67.

The "usage environment log data" here is data indicating what sound pressure level is inputted, and for how long, from the microphone 61 of the hearing aid 51 when each of the memories is used.

The record in the usage environment log data storage section 67 holds the results for one week. In this embodiment, the sound pressure level is used to describe the usage environment log data, but determination of the level range can also be replaced with the result of sound environment identification using an HMM (hidden Markov model), for example.

FIG. 15 shows that during use in a normal state, a level range 1 was 10%, a level range 2 was 70%, a level range 3 was 15%, a level range 4 was 5%, a level range 5 was 0%, and a level range 6 was 0% when the input section 70 of the hearing aid 51 was operated so as to select a state in which hearing aid processing was handled with the adjustment value parameters of the memory 68a in the hearing aid processor 65.

When the user was watching television, the level range 1 was 0%, the level range 2 was 5%, the level range 3 was 30%, the level range 4 was 30%, the level range 5 was 30%, and the level range 6 was 5% when the input section 70 of the hearing aid 51 was operated so as to select a state in which hearing aid processing was handled with the adjustment value parameters of the memory 68b in the hearing aid processor 65.

When the user was listening to music, the level range 1 was 0%, the level range 2 was 0%, the level range 3 was 20%, the level range 4 was 70%, the level range 5 was 10%, and the level range 6 was 0% when the input section 70 of the hearing aid 51 was operated so as to select a state in which hearing aid processing was handled with the adjustment value parameters of the memory 68c in the hearing aid processor 65.

When the user was riding a train, the level range 1 was 0%, the level range 2 was 0%, the level range 3 was 0%, the level range 4 was 0%, the level range 5 was 20%, and the level range 6 was 80% when the input section 70 of the hearing aid 51 was operated so as to select a state in which hearing aid processing was handled with the adjustment value parameters of the memory 68d in the hearing aid processor 65.

The term "level range" means the range of the sound pressure level. The level ranges 1 to 6 shown in FIG. 15 indicate that the sound pressure level increases from level range 1 to level range 6 in that order.

For example, the level range 1 is 0 to 48 dB SPL, the level range 2 is a sound pressure level of 48 to 60 dB SPL, the level range 3 is a sound pressure level of 60 to 72 dB SPL, the level range 4 is a sound pressure level of 72 to 84 dB SPL, the level range 5 is a sound pressure level of 84 to 96 dB SPL, and the level range 6 is a sound pressure level of 96 dB SPL and up.

The state shown in FIG. 15 cannot necessarily be considered a problematic situation in the use of the hearing aid 51, but it can be seen that the inside of the train in which the user 52 is present is quite noisy, and this should be kept in mind in readjusting the hearing aid 51.

As shown in FIG. 8, in readjusting the hearing aid 51, the hearing aid 51 is connected to the fitting PC 55 via the connector box 54 of the fitting device 53. The fitting PC 55 is connected to the Web shared server 58.

Then, the hearing ability data for the user 52 from the adjustment value data storage section 68, the basic label 72a, television label 72e, music label 72f, and train label 72c stored in the four memories 68a, 68b, 68c, and 68d, and the various adjustment value parameters are read by the hearing aid reader 76. The hearing aid reader 76 reads out the usage environment log data shown in FIG. 15 from the usage environment log data storage section 67 (S5 in FIG. 11c).

The hearing ability data for the user 52, the basic label 72a, television label 72e, music label 72f, and train label 72c stored in the four memories 68a, 68b, 68c, and 68d, the various adjustment value parameters, and the usage environment log data shown in FIG. 15 thus acquired are then recorded to the adjustment value memory 70a.

After this, the hearing ability data for the user 52, the basic label 72a, television label 72e, music label 72f, and train label 72c stored in the four memories 68a, 68b, 68c, and 68d, the various adjustment value parameters, and the usage environment log data shown in FIG. 15 are sent from the server transmitter 74 to the Web shared server 58 (S6 in FIG. 11c).

At the Web shared server 58, the data receiver 76a receives this information and stores it in the client data storage section 80 via the data storage section 78. The close user determination section 79 extracts a user close to the user 52 hearing ability data sent from the fitting device 53 (similarity in FIG. 11c, and step 1 in FIGS. 10 and 14).

In the extraction of a user whose hearing ability data is close, the hearing ability values at various frequencies are expressed as vectors, and the top N people at the distance between vectors are termed close users, among other such methods that can be used. Here, a range of 1 to 3 kHz may be weighted, etc., to emphasize the conversation band, for example.

Figure 14:
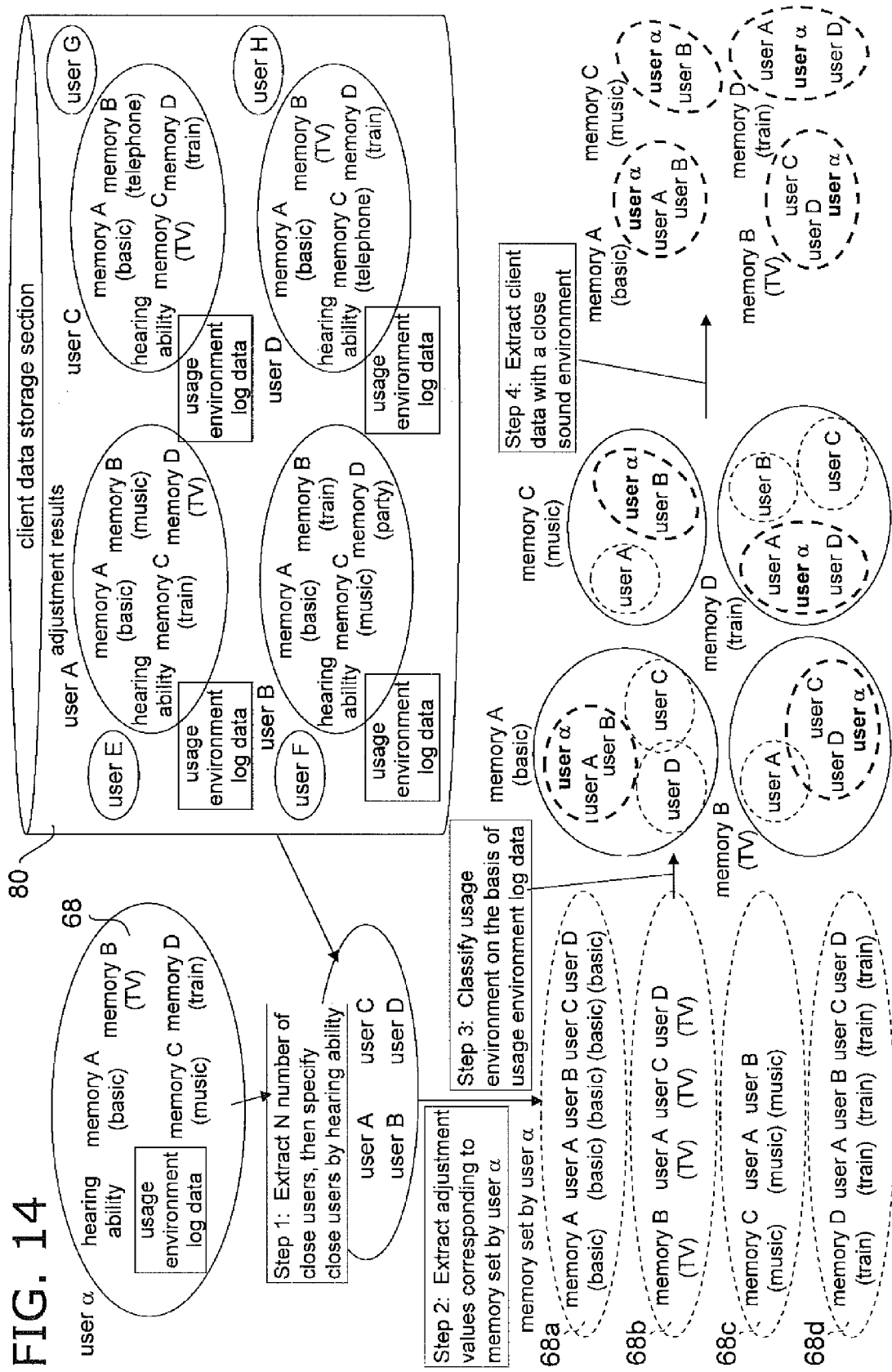
FIG. 14 is a diagram of the operating state of the hearing aid fitting system in FIG. 8.

In FIG. 14, the user 52 is referred to as user α.

N number of people, including user A, user B, user C, and user D, are extracted from the client data storage section 80 as people having a hearing ability close to the hearing ability of user α.

Then, at the memory-specific adjustment value extractor 81, adjustment value parameters are extracted for each of the usage environments corresponding to the plurality of usage environments set by the user in the adjustment value data storage section 68, from among the plurality of usage environments that the extracted user A, user B, user C, and user D have set in the adjustment value data storage section 68 (S8 in FIG. 11c, step 2 in FIGS. 10 and 14).

As discussed above, the basic label 72a is set in the memory 68a, the television label 72e in the memory 68b, the music label 72f in the memory 68c, and the train label 72c in the memory 68d for the user 52 (user α). A basic label, a music label, a train label, and a television label are set for user A. A basic label, a music label, a train label, and a party label are set for user B. A basic label, a train label, a train label, and a television label are set for user C. And A basic label, a train label, a telephone label, and a television label are set for user D.

Therefore, four people (user A, user B, user C, and user D) are extracted for the adjustment of the basic label 72a of the user 52. Three people (user A, user C, and user D) are extracted for the adjustment of the television label 72e. Two people (user A and user B) are extracted for the adjustment of the music label 72f. And four people (user A, user B, user C, and user D) are extracted for the adjustment of the train label 72c.

As discussed above, the description here was for four people, namely, user A, user B, user C, and user D, for the sake of convenience, but in actual practice a corresponding number of people are extracted from among the N number of close users.

Next, at the usage environment clustering section 82 and the usage environment similar user specifier 83, adjustment value parameters are extracted for every usage environment that is close to the usage environment log data for the user 52 (user α) from the adjustment value parameters for every extracted usage environment (S9 and S10 in FIG. 11c, step 3 in FIGS. 10 and 14).

More specifically, first the usage environment clustering section 82 clusters the usage environment log data for the memory corresponding to the person set in the same memory as the memory extracted above.

The clustering here can be accomplished by a k-means method, with the log data for the corresponding memory being replaced with a vector expression. The vector expression can be accomplished by using the ratio of each level range as an element. For example, the log data of the memory 68a for the user 52 can be expressed as (0.1, 0.7, 0.15, 0.05, 0, 0).

The usage environment similar user specifier 83 may specify a person belonging to the same cluster as the user 52, from the clustering results obtained by the k-means method.

As a result, user A and user B are extracted as people having usage environment log data that are close to the basic label 72a (memory 68a) for the user 52 (user α). Also, user C and user D are extracted as people having usage environment log data that are close to the television label 72e (memory 68b) for the user 52 (user α). Further, user B is extracted as a person having usage environment log data that are close to the music label 72f (memory 68c) for the user 52 (user α). Further, user A and user D are extracted as people having usage environment log data that are close to the train label 72c (memory 68d) for the user 52 (user α).

The data thus extracted are sent from the data transmitter 77 to the server receiver 75 and stored in the adjustment value memory 70a (S11 in FIG. 11c).

Next, the adjustment value parameters for every extracted usage environment received by the server receiver 75 are displayed on the display section 57 of the fitting device 53.

Figure 16:
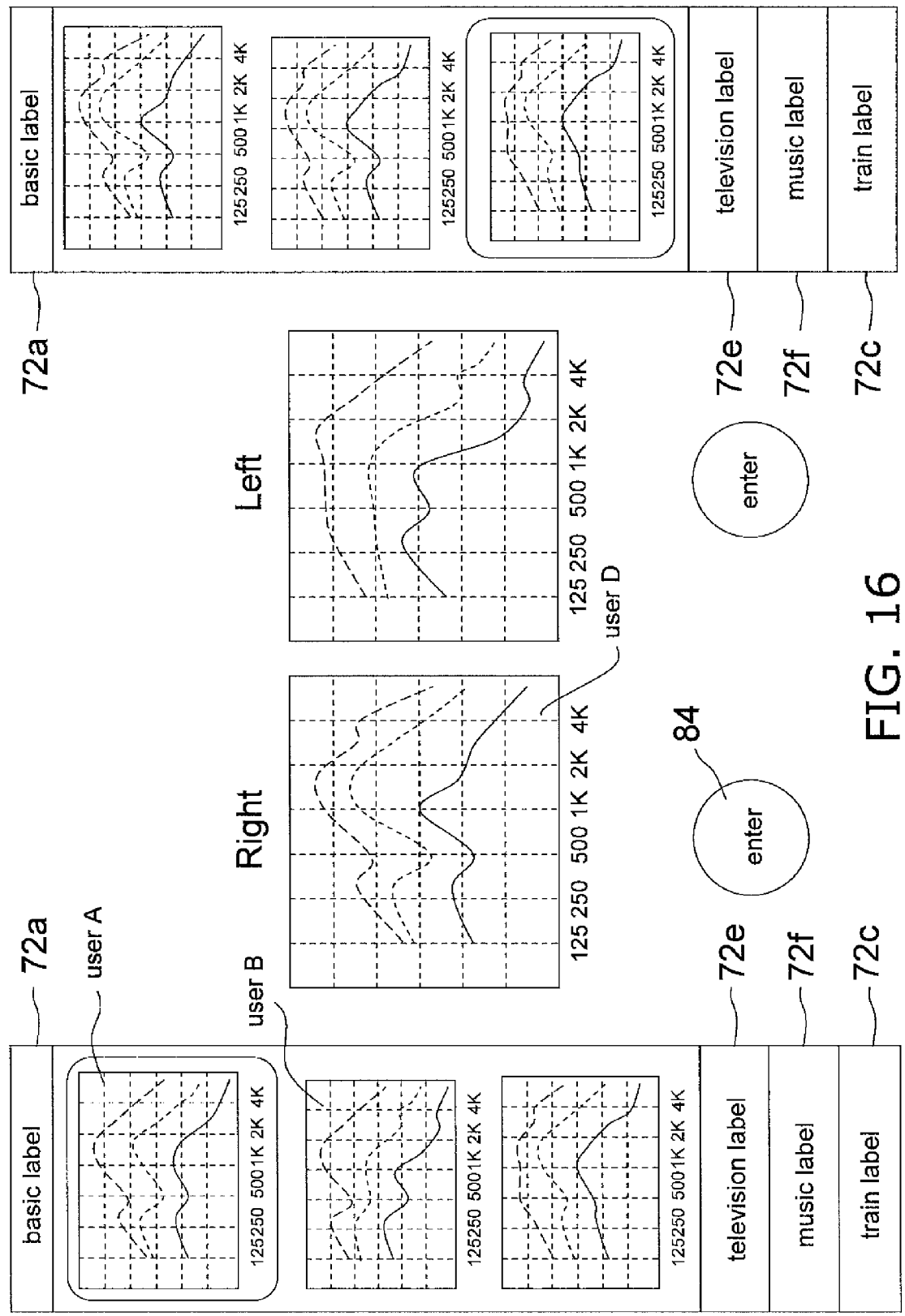
FIG. 16 is a diagram of the operating state of the hearing aid fitting system in FIG. 8.

FIG. 16 shows the display screen of the display section 57, which shows the adjustment state with respect to the basic label 72a (memory 68a).

In FIG. 16, data for left and right hearing aids 51 are displayed on the display section 57 in order to readjust the left and right hearing aids 51, but for the sake of simplicity, only the hearing aid 51 used for the right ear will be explained. The left hearing aid may then be readjusted in the same way.

As shown in FIG. 16, adjustment value parameters corresponding to the basic label 72a (memory 68a) for user A and user B are displayed on the display section 57 as people having usage environment log data that is close to the basic label 72a (memory 68a) for the user 52 (user α).

Therefore, the adjusting technician 60 tests the user 52 by using the adjustment value parameters corresponding to the basic label 72a (memory 68a) for the current user 52 himself. Next, the adjusting technician 60 has the user 52 listen to the adjustment value parameters corresponding to the basic label 72a (memory 68a) for user A and user B, and selects those adjustment value parameters that are the best for the user 52.

Next, the adjusting technician 60 presses an enter button 84 (FIG. 16) to write the selected adjustment value parameters to the memory 68a of the adjustment value data storage section 68 via the adjustment value rewriter 69 and the hearing aid writer 73, which completes the readjustment (S12 in FIG. 11c).

Figure 17:
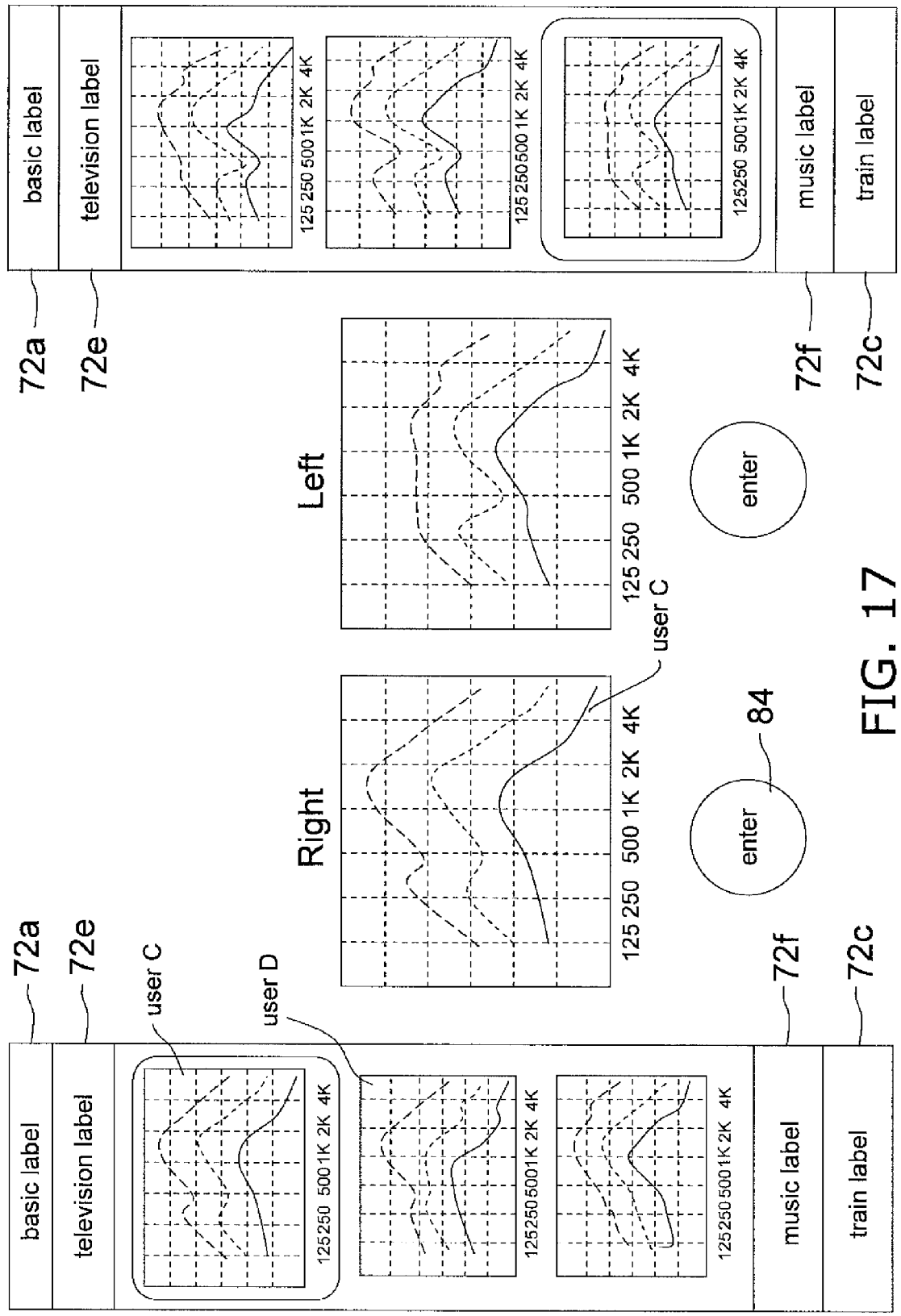
FIG. 17 is a diagram of the operating state of the hearing aid fitting system in FIG. 8.

Then, as shown in FIG. 17, the data for the next television label 72e (memory 68b) are displayed. More specifically, adjustment value parameters corresponding to the basic label 72a (memory 68a) for user C and user D are displayed on the display section 57 as people having usage environment log data that is close to the television label 72e (memory 68b) for the user 52 (user α).

Therefore, the adjusting technician 60 tests the user 52 by using the adjustment value parameters corresponding to the television label 72e (memory 68b) for the current user 52 himself, and then tests the user 52 using the adjustment value parameters corresponding to the television label 72e (memory 68b) for user C and user D, and selects those adjustment value parameters that are the best for the user 52.

Next, the adjusting technician 60 presses the enter button 84 (FIG. 16) to write the adjustment value parameters selected by the user 52 to the memory 68b of the adjustment value data storage section 68 via the adjustment value rewriter 69 and the hearing aid writer 73, which completes the readjustment (S12 in FIG. 11c).

Thereafter, the adjusting technician 60 performs readjustment of the music label 72f (memory 68c) and the train label 72c (memory 68d) in the same manner.

With this embodiment, readjustment of the hearing aid 51 can be performed easily and in a short time, and according to the actual usage environment of the user 52. Furthermore, the data utilized in this are data for other people with similar actual usage environments and hearing ability similar to that of the user 52, so the results after readjustment will be extremely satisfactory to the user 52.

A hearing aid setting program of the present invention causes a computer to execute a hearing aid fitting method comprising:

processing in which a plurality of hearing adjustment result data with respect to a plurality of hearing ability data similar to the hearing ability data of the hearing aid user are specified and pulled out from a client data storage section;

processing in which representative hearing adjustment result data are selected from among each of a plurality of clusters in which a plurality of the pulled out hearing adjustment result data are classified;

processing in which data that are optimal for the hearing aid user are selected as an initial adjustment candidate from among the plurality of representative hearing adjustment result data; and processing in which the hearing adjustment result data of the initial adjustment candidate are fine tuned so as to better match the hearing aid user.

The hearing aid setting program of the present invention further comprises processing in which a plurality of previously stored hearing adjustment result data are classified into a plurality of clusters on the basis of similarity.

A hearing aid adjustment program of the present invention makes use of a fitting device connected to a server, and causes a computer to execute a hearing aid fitting method comprising:

a transmission step of transmitting hearing ability data, usage environment log data, and adjustment value parameters for the hearing aid user from the fitting device to the server;

a first extraction step of extracting users close to the hearing ability data of the hearing aid user transmitted in the transmission step;

a second extraction step of extracting adjustment value parameters for every usage environment, corresponding to a plurality of usage environments set by the hearing aid user, from among a plurality of usage environments set by the users extracted in the first extraction step;

a third extraction step of extracting adjustment value parameters for every usage environment close to the usage environment log data for the hearing aid user, from among adjustment value parameters for every usage environment extracted in the second extraction step;

a step of transmitting adjustment value parameters for every extracted usage environment from the server to the fitting device; and a step of supplying the adjustment value parameters for every usage environment extracted in the third extraction step from the fitting device to the hearing aid.

A hearing aid adjustment program of the present invention uses a fitting device to adjust a hearing aid, and causes a computer to execute a hearing aid fitting method comprising:

a transmission step of transmitting hearing ability data, usage environment log data, and adjustment value parameters for the hearing aid user from the fitting device;

a first extraction step of extracting users close to the hearing ability data of the hearing aid user transmitted in the transmission step;

a second extraction step of extracting adjustment value parameters for every usage environment, corresponding to a plurality of usage environments set by the hearing aid user, from among a plurality of usage environments set by the users extracted in the first extraction step;

a third extraction step of extracting adjustment value parameters for every usage environment close to the usage environment log data for the hearing aid user, from among adjustment value parameters for every usage environment extracted in the second extraction step;

a step of transmitting adjustment value parameters for every extracted usage environment extracted in the third extraction step, to the fitting device; and a step of supplying the adjustment value parameters for every usage environment extracted in the third extraction step from the fitting device to the hearing aid.

The hearing aid adjustment program can constitute a hearing aid fitting device or a hearing aid fitting system by being installed to any personal computer or the like, by downloading through a communication line, etc., from a CD-ROM or other such storage medium, for example.

The hearing aid fitting system of the present invention is constituted so as to include a server and a hearing aid fitting device connected to a hearing aid, comprising:

an input section to which hearing ability data for a hearing aid user are inputted;

a hearing aid reader that reads, from the hearing aid, usage environment log data for each of a plurality of types of usage environment and adjustment value parameters for each of the plurality of types of usage environment;

a server transmitter that transmits the hearing ability data, the usage environment log data, and the adjustment value parameters to the server;

a server that extracts users close to the hearing ability data for the hearing aid user transmitted from the server transmitter, extracts adjustment value parameters for every usage environment corresponding to a plurality of usage environments set by the hearing aid user from among a plurality of usage environments set by the extracted users, and extracts and transmits adjustment value parameters for every usage environment close to the usage environment log data of the hearing aid user from among the adjustment value parameters for every extracted usage environment;

a server receiver that receives adjustment value parameters for each of a plurality of types of usage environment extracted and transmitted by the server; and a hearing aid writer that writes the adjustment value parameters to an adjustment value data storage section of the hearing aid.

With the hearing aid fitting system of the present invention, a server connected to a hearing aid adjustment device extracts users close to the hearing ability data for the hearing aid user transmitted from the hearing aid, extracts adjustment value parameters for every usage environment corresponding to a plurality of usage environments set by the hearing aid user from among a plurality of usage environments set by the extracted users, extracts adjustment value parameters for every usage environment close to the usage environment log data of the hearing aid user from among the adjustment value parameters for every extracted usage environment, and sends these back to the hearing aid, and writes them to the hearing aid, so adjustment value parameters for every usage environment of the hearing aid user can be set extremely easily according to the usage environment of that user. As a result, satisfaction on the part of the user with respect to the hearing aid settings can be improved.

Other Embodiments (A)

In Embodiments 1 to 3 above, examples were described in which the client data storage sections 10 and 110 were included in the hearing aid fitting device, but the present invention is not limited to or by this.

For example, an external storage device that is connected to the hearing aid fitting device or hearing aid fitting system, storage located on the Internet, or the like may be used as a client data storage section.

(B)

In Embodiment 4 above, an example was described in which the client data storage section 80, the close user determination section 79, the usage environment clustering section 82, and so forth were located on the Web shared server 58, and various processing was executed at the Web shared server 58, but the present invention is not limited to or by this.

For example, as in Embodiments 1 to 3 above, a client data storage section, a close user determination section, a usage environment clustering section, or the like may be provided within the hearing aid fitting device, and the processing executed at the Web shared server 58 described in Embodiment 4 above may be executed within the hearing aid fitting device.

In this case, the client data storage section does not necessarily have to be provided within the hearing aid fitting device, and may be provided to an external storage device connected to the hearing aid fitting device, for example.

(C)

In Embodiments 1 to 3 above, an example was described in which hearing aid fitting was performed by testing the user for speech and so forth processed on the basis of representative hearing adjustment result data, from among a plurality of clusters in which a plurality of hearing adjustment result data corresponding to various hearing ability levels are classified on the basis of similarity, but the present invention is not limited to or by this.

For example, adjustment based on the usage environments described in Embodiment 4 above may be incorporated into the processing described in Embodiments 1 to 3 above.

Consequently, hearing aid fitting can be performed that is more comfortable for the hearing aid user and that takes the user's preferences and usage environments into account.

INDUSTRIAL APPLICABILITY

With the present invention, hearing aid usage setup can be performed in a short time, and can be performed in a state corresponding to actual usage situations, so the present invention is expected to find wide application as a hearing aid fitting device.

REFERENCE SIGNS LIST 1 hearing aid fitting device
2 input section
3 display section
4 hearing aid
5 connector box
6, 7 wiring
8 user
9 adjusting technician
10 client data storage section
11 close user determination section
12 hearing ability input section
13 clustering section
14 representative characteristic determination section
15 initial adjustment candidate selector
16 fine tuner
17 adjustment value input section
18 adjustment value rewriter
19 hearing aid writer
20 main adjustment value memory
21 enter button
51 hearing aid
52 user
53 fitting device (hearing aid fitting device)
54 connector box
55 fitting PC
56 input section
57 display section
58 Web shared server
59 network
60 adjusting technician
61 microphone
62 receiver
63 A/D converter
64 sound environment identifier
65 hearing aid processor
66 D/A converter
67 usage environment log data storage section
68 adjustment value data storage section
69 adjustment value rewriter
70 input section
70a adjustment value memory
71 basic difference data storage section
72 memory label storage section
73 hearing aid writer
74 server transmitter
75 server receiver
76 hearing aid reader
76a data receiver
77 data transmitter
78 data storage section
79 close user determination section
80 client data storage section
81 memory-specific adjustment value extractor
82 usage environment clustering section
83 usage environment similar user specifier
84 enter button
110 client class data storage section

The invention claimed is:

1. A hearing aid fitting device, comprising:
a hearing ability input section for inputting hearing ability data of a user;
a representative characteristic determination section configured to extract, as representative characteristics, representative hearing adjustment result data from each cluster classified on the basis of a similarity of a plurality of hearing adjustment result data corresponding to a plurality of hearing ability data similar to the hearing ability data inputted with the hearing ability input section;
an initial adjustment candidate selector that switches between and outputs as aural characteristics a plurality of the representative hearing adjustment result data extracted as the representative characteristics by the representative characteristic determination section, and prompts for a selection of one of the plurality of the representative hearing adjustment result data that is optimal for the user; and
a fine tuner with which the hearing adjustment result data selected from the plurality of the representative hearing adjustment result data switched between by the initial adjustment candidate selector are fine tuned for further compatibility with the user.

2. The hearing aid fitting device according to claim 1, further comprising:
a close user determination section with which a plurality of hearing adjustment result data corresponding to a plurality of hearing ability data similar to the hearing ability data inputted with the hearing ability input section are specified and pulled out from a client data storage section that stores a plurality of hearing adjustment result data corresponding to a plurality of hearing ability data; and a clustering section with which the plurality of the hearing adjustment result data pulled out with the close user determination section are classified on the basis of a similarity.

3. The hearing aid fitting device according to claim 1, wherein a plurality of clusters classified ahead of time on the basis of a similarity for each of hearing ability data, and representative hearing adjustment result data corresponding to the plurality of clusters are stored ahead of time in a client data storage section, and the representative characteristic determination section extracts the representative hearing adjustment result data from the client data storage section from among the plurality of clusters corresponding to the inputted hearing ability data.

4. The hearing aid fitting device according to claim 1, further comprising a client data storage section that stores hearing adjustment result data corresponding to a plurality of hearing ability data ahead of time.

5. A hearing aid fitting device comprising:

a hearing ability input section for inputting hearing ability data of a user;

a representative characteristic determination section configured to extract, as representative characteristics, representative hearing adjustment result data from each cluster classified on the basis of a similarity of a plurality of hearing adjustment result data corresponding to a plurality of hearing ability data similar to the hearing ability data inputted with the hearing ability input section;

an initial adjustment candidate selector that switches between and outputs as aural characteristics a plurality of the representative hearing adjustment result data extracted as the representative characteristics by the representative characteristic determination section, and prompts for a selection of one of the plurality of the representative hearing adjustment result data that is optimal for the user; and a fine tuner with which the hearing adjustment result data selected from the plurality of the representative hearing adjustment result data switched between by the initial adjustment candidate selector are fine tuned for further compatibility with the user, wherein the fine tuner has an adjustment value input section for inputting an adjustment value for fine tuning the selected hearing adjustment result data, an adjustment value rewriter to which the adjustment value is inputted from the adjustment value input section and which fine tunes the selected hearing adjustment result data on the basis of the adjustment value and rewrites the fine-tuned hearing adjustment result data, and a hearing aid writer that writes the fine-tuned hearing adjustment result data rewritten by the adjustment value rewriter to a hearing aid.

6. A hearing aid fitting device comprising:

a hearing ability input section for inputting hearing ability data of a user;

a representative characteristic determination section configured to extract, as representative characteristics, representative hearing adjustment result data from each cluster classified on the basis of a similarity of a plurality of hearing adjustment result data corresponding to a plurality of hearing ability data similar to the hearing ability data inputted with the hearing ability input section;

an initial adjustment candidate selector that switches between and outputs as aural characteristics a plurality of the representative hearing adjustment result data extracted as the representative characteristics by the representative characteristic determination section, and prompts for a selection of one of the plurality of the representative hearing adjustment result data that is optimal for the user; and a fine tuner with which the hearing adjustment result data selected from the plurality of the representative hearing adjustment result data switched between by the initial adjustment candidate selector are fine tuned for further compatibility with the user, wherein the representative characteristics are representative hearing adjustment result data included in each cluster which a plurality of hearing adjustment result data associated with a plurality of hearing ability data similar to the hearing ability data inputted with the hearing ability input section is classified on the basis of the similarity.

* * * * *